(12) United States Patent
Unsai (10) Patent No.: US 10,499,799 B2
(45) Date of Patent: Dec. 10, 2019

(54) IMAGE PICKUP UNIT AND ENDOSCOPE (71) Applicant: OLYMPUS CORPORATION, Tokyo (JP)

(72) Inventor: Hiroshi Unsai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/037,104

(22) Filed: Jul. 17, 2018

(65) Prior Publication Data

US 2018/0317756 A1 Nov. 8, 2018

Related U.S. Application Data (63) Continuation of application No. PCT/JP2017/014959, filed on Apr. 12, 2017.

(30) Foreign Application Priority Data

Jun. 7, 2016 (JP) .................................. 2016-113778

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00096* (2013.01); *A61B 1/00124* (2013.01);
(Continued)

(58) Field of Classification Search
CPC . A61B 1/051; A61B 1/00096; A61B 1/00124; G02B 23/24; G02B 23/2423; G02B 23/243; G02B 23/2484; H04N 5/2253; H04N 5/2254; H04N 5/369; H04N 2005/2255; H05K 2201/10151
See application file for complete search history.

(56) References Cited

U.S. PATENT DOCUMENTS

2011/0249106 A1* 10/2011 Makino ................ H04N 5/2254
348/76
2012/0197081 A1* 8/2012 Kimura .............. A61B 1/00124
600/110
(Continued)

FOREIGN PATENT DOCUMENTS

EP 2614766 A1 7/2013
EP 2944248 A1 11/2015
(Continued)

OTHER PUBLICATIONS

International Search Report dated Jun. 20, 2017 issued in PCT/JP2017/014959.

Primary Examiner — John R Schnurr
(74) Attorney, Agent, or Firm — Scully, Scott, Murphy & Presser, P.C.

(57) ABSTRACT

An image pickup unit of the present invention includes an image sensor, a connection board, a circuit board, a cable, and protection material. If an external force acts in a direction orthogonal to an extension direction of the cable, the whole of the circuit board, which is a rigid body, is displaced relative to an electrode portion of the image sensor by the external force. In response to the displacement of the circuit board, the connection board is displaced so that a curve radius of a curved portion changes, between a first land portion connected to the image sensor and a second land portion connected to the circuit board, and thereby a load by the external force transmitted to the image sensor from the cable through the circuit board is reduced.

5 Claims, 7 Drawing Sheets (51) Int. Cl.
*H04N 5/225* (2006.01)
*H04N 5/369* (2011.01)
*G02B 23/24* (2006.01)

(52) U.S. Cl.
CPC ....... *G02B 23/243* (2013.01); *G02B 23/2423* (2013.01); *G02B 23/2484* (2013.01); *H04N 5/2253* (2013.01); *H04N 5/2254* (2013.01); *H04N 5/369* (2013.01); *H04N 2005/2255* (2013.01); *H05K 2201/10151* (2013.01)

(56) References Cited

U.S. PATENT DOCUMENTS

| | | |
|---|---|---|
| 2013/0188030 A1 | 7/2013 | Igarashi |
| 2015/0312457 A1* | 10/2015 | Kojima .............. G02B 23/2484 348/76 |
| 2015/0378144 A1 | 12/2015 | Handte et al. |
| 2017/0172388 A1* | 6/2017 | Ohno ................. A61B 1/00124 |

FOREIGN PATENT DOCUMENTS

| | | | |
|---|---|---|---|
| JP | H10-033474 A | 2/1998 | |
| JP | H11-216102 A | 8/1999 | |
| JP | H11-252418 A | 9/1999 | |
| JP | 2011-200398 A | 10/2011 | |
| JP | 2012-055570 A | 3/2012 | |
| JP | 2014-133046 A | 7/2014 | |
| WO | WO 2012/032934 A1 | 3/2012 | |
| WO | PCT/JP2013/074691 * | 7/2014 | ........... H04N 5/2257 |
| WO | WO 2014/109094 A1 | 7/2014 | |
| WO | WO 2014/125070 A1 | 8/2014 | |

* cited by examiner

IMAGE PICKUP UNIT AND ENDOSCOPE

CROSS REFERENCE TO RELATED APPLICATION

This application is a continuation application of PCT/JP2017/014959 filed on Apr. 12, 2017 and claims benefit of Japanese Application No. 2016-113778 filed in Japan on Jun. 7, 2016, the entire contents of which are incorporated herein by this reference.

BACKGROUND OF THE INVENTION

1. Field of the Invention

The present invention relates to an image pickup unit in which a rigid circuit board is connected to an electrode portion of an image sensor.

2. Description of the Related Art

In general, an image pickup unit is configured as a unit in which a circuit board for driving and signal processing is connected to an image sensor for which a solid image pickup device such as a CCD or a CMOS is used. In the case of mounting such an image pickup unit, for example, in an endoscope an elongated insertion portion of which is inserted into a subject/object to pick up an image of an observation site, it is often a case that a flexible board is used as a circuit board, and a cable is connected to the flexible board to connect to an external apparatus, as disclosed in Japanese Patent Application Laid-Open Publication No. H10-33474, for example.

Nowadays, the image sensor is often formed with a small and lightweight chip size package on which high density implementation is possible. On the chip size package, an image pickup surface of an image pickup device is arranged on a front face side of the package, and an electrode portion of the image pickup device is arranged on a back face of the package.

Further, in order to improve heat resistance and mechanical strength of the circuit board, a rigid circuit board such as a ceramic board is often used. In the case of connecting the ceramic board to the electrode portion of the chip size package, the board can be directly connected via a solder ball forming a bump on the back face of the package.

Figure 8:
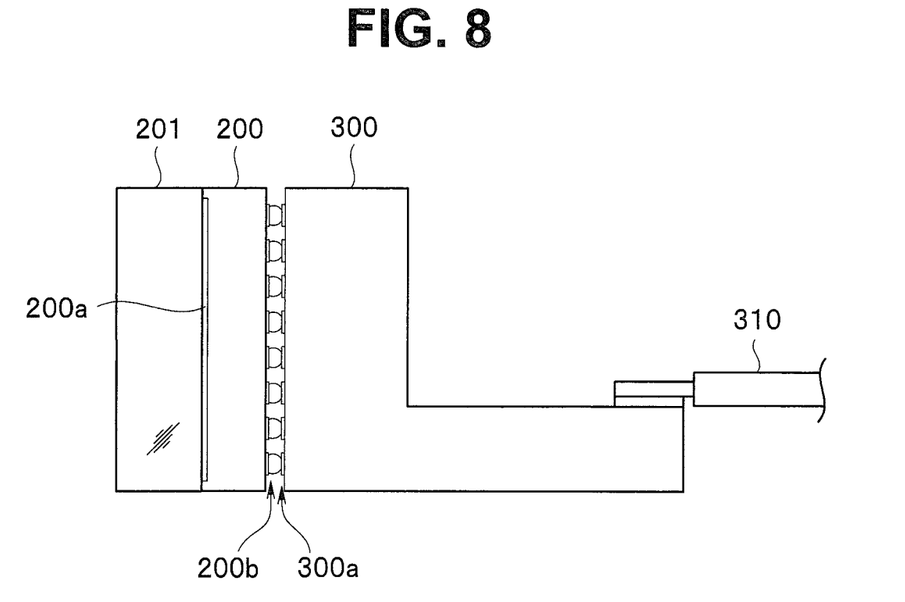
FIG. 8 is an explanatory diagram showing a conventional image pickup unit.

In the case of including such a chip size package image sensor in a distal end portion of an endoscope, for example, as shown in FIG. 8, a glass lid 201 for protection is bonded to a front face side of the package where an image pickup surface 200a of an image sensor 200 is arranged, with adhesive or the like; furthermore, a cover glass for positioning (not shown) is bonded to the glass lid 201; and the cover glass is held by a holding frame (not shown) arranged in the distal end portion of the endoscope.

Then, an electrode portion 300a of a ceramic board 300 is bonded to an electrode portion 200b on a package back face of the image sensor 200. And a cable 310 is connected to a proximal end side of the ceramic board 300 and extended on an operation portion side of the endoscope. In a peripheral part from the electrode portion 200b of the image sensor 200 to the ceramic board 300, resin material is filled and fixed.

SUMMARY OF THE INVENTION

An image pickup unit according to an aspect of the present invention includes: an image sensor including an image pickup device package, an image pickup surface of an image pickup device being arranged on a front face side of the package, and an electrode portion of the image pickup device being arranged on a back face of the package; a connection board including a first land portion and a second land portion, the first land portion being connected to the electrode portion of the image sensor; a rigid circuit board including a first connection portion and a second connection portion, the first connection portion being connected to the second land portion of the connection board; a cable connected to the second connection portion of the circuit board; and protection material arranged around the connection board and the image sensor; wherein the image sensor and the circuit board are arranged such that the electrode portion of the image sensor and the first connection portion face each other; the connection board includes a curved portion between the first land portion and the second land portion, the curved portion being curved in a manner of being displaceable by an external force transmitted from the cable via the circuit board; and the protection material includes first protection material and second protection material softer than the first protection material, the second protection material being arranged at least inside the curved portion.

DETAILED DESCRIPTION OF THE PREFERRED EMBODIMENTS

Embodiments of the present invention will be described below with reference to drawings.

First Embodiment

Figure 1:
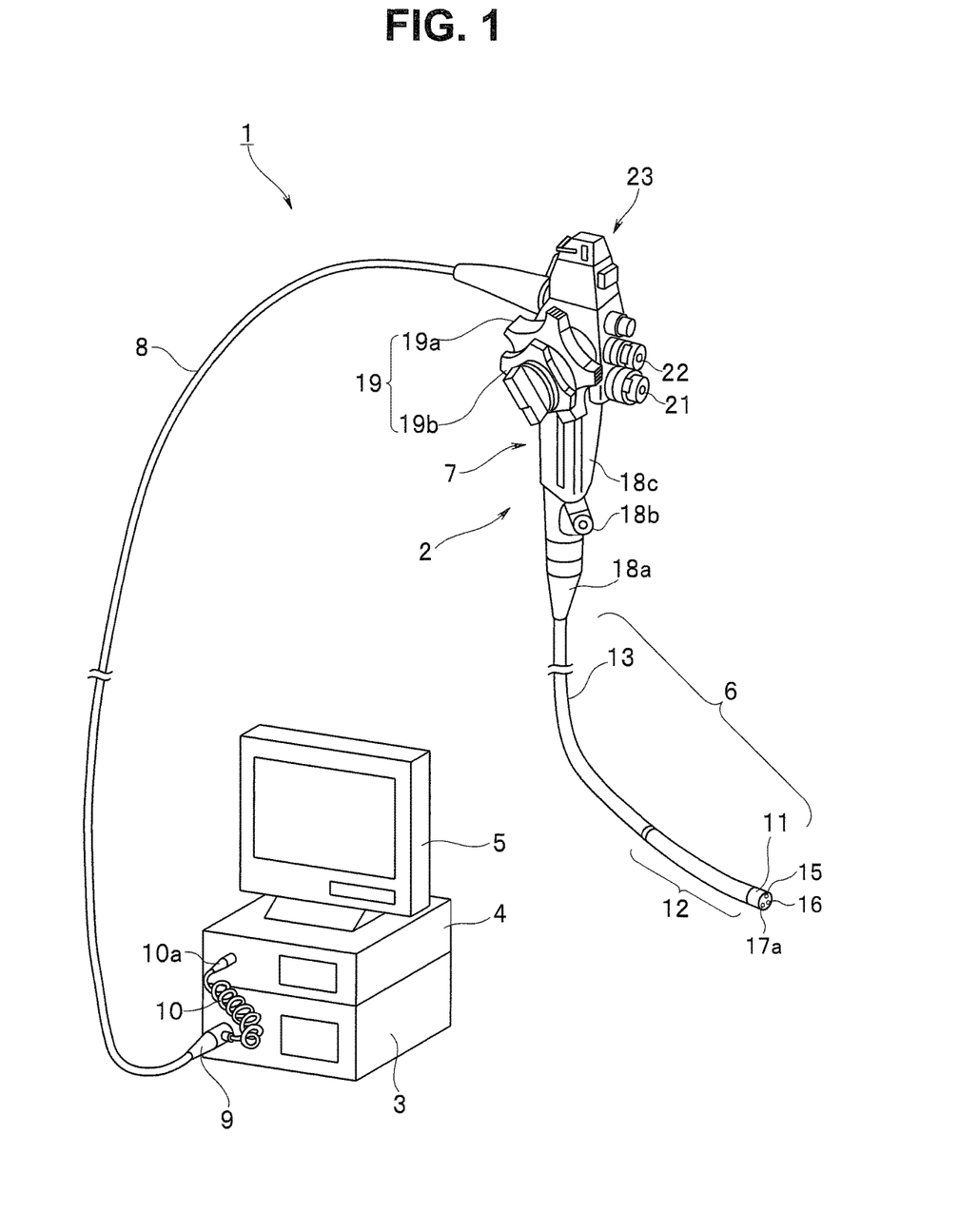
FIG. 1 is a configuration diagram of an endoscope apparatus according to a first embodiment of the present invention.

FIG. 1 shows an example of an endoscope apparatus to which the present invention is applied. In the present embodiment, an endoscope apparatus 1 is configured being provided with an endoscope 2 including an image pickup unit, a light source device 3 configured to supply illuminating light to the endoscope 2, a video processor 4 as a signal processing device configured to perform signal processing for the image pickup unit mounted in the endoscope 2, and a color monitor 5 as a display device configured to display an endoscopic image.

The endoscope 2 includes an elongated insertion portion 6 to be inserted into a subject/object, an operation portion 7 provided on a proximal end of the insertion portion 6, a universal cord 8 extended from the operation portion 7, and an endoscope connector 9 provided on an end portion of the universal cord 8. By the endoscope connector 9 being detachably connected to the light source device 3, illuminating light from the light source device 3 is supplied to a light guide not shown in the endoscope 2. One end of a connection cable 10 is connected to the endoscope connector 9, and an electrical connector 10a provided on the other end of the connection cable 10 is detachably connected to the video processor 4. The video processor 4 is connected to the color monitor 5 via a video cable not shown.

The insertion portion 6 of the endoscope 2 is configured being provided with a rigid distal end portion 11 provided on a distal end, a bendable bending portion 12 provided on a rear end of the distal end portion 11, and a flexible tube portion 13 having flexibility of extending from a rear end of the bending portion 12 to a front end of the operation portion 7.

Figure 2:
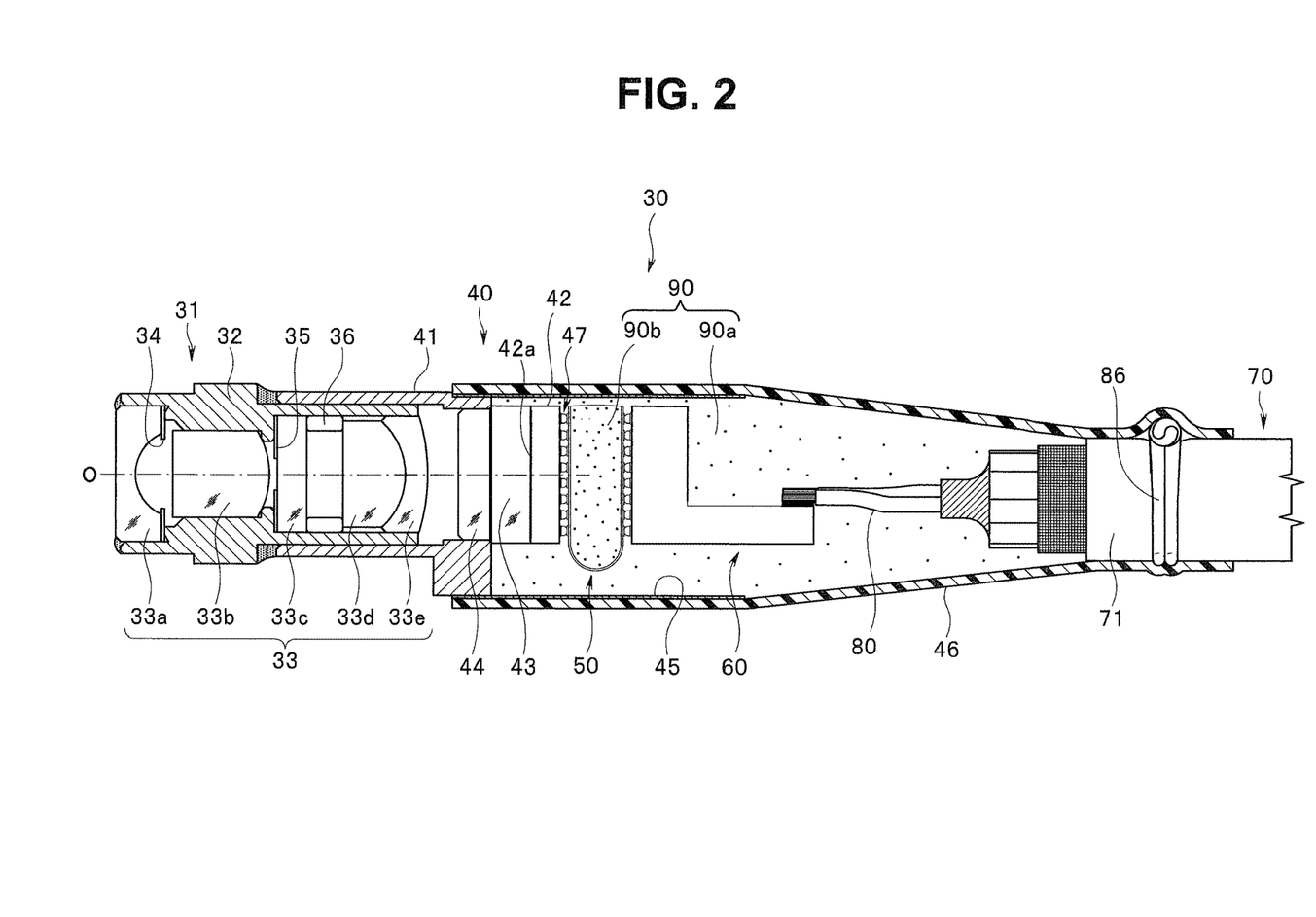
FIG. 2 is an explanatory diagram showing an image pickup unit provided in a distal end portion of an endoscope according to the first embodiment of the present invention.

On a distal end face of the distal end portion 11, an observation window 15, a plurality of illumination windows 16 (FIG. 1 shows only one), a distal end opening 17a of a treatment instrument channel (not shown), and a nozzle for cleaning not shown. On an inner side (a rear face side) of the observation window 15, an image pickup unit 30 provided in the distal end portion 11 is arranged as shown in FIG. 2.

Illumination lenses are attached to the illumination windows 16, and a light guide for transmitting illuminating light from the light source device 3 is arranged being connected to the illumination lenses (neither the illumination lenses nor the light guide is shown). Illuminating light transmitted by the light guide is emitted to a front side of the distal end face via the illumination lenses, and thereby an observation target site in a subject/object, which is a visual field range of the image pickup unit 30, is illuminated.

The operation portion 7 is provided with a bend preventing portion 18a for a part from which the proximal end of the insertion portion 6 is extended, a treatment instrument insertion port 18b arranged on a side portion on a lower part side, an operation portion body 18c constituting a grip portion provided on a middle part, a bending operation portion 19 provided on an upper part side and including two bending operation knobs 19a and 19b, an air/water feeding control portion 21, a suction control portion 22, and a switch portion 23 including a plurality of switches, the switch portion 23 being mainly for operating an image pickup function.

Note that inside the operation portion 7, the treatment instrument insertion port 18b of the operation portion 7 communicates with the treatment instrument channel made inside the insertion portion 6, and is open at the distal end opening 17a of the distal end portion 11.

Next, the image pickup unit 30 arranged inside the distal end portion 11 of the endoscope 2 will be described based on FIG. 2.

The image pickup unit 30 is arranged being inserted through a distal end rigid member forming the distal end portion 11, and is fixed to the distal end rigid member with screws or the like from a side face direction. The image pickup unit 30 is configured including an observation optical system unit 31 constituting an objective optical system including the observation window 15, and an image pickup device unit 40 as an image pickup portion arranged being connected to a rear end side of the observation optical system unit 31.

In the present embodiment, the observation optical system unit 31 is configured including a lens frame 32 holding lenses and a lens group 33 including a plurality of fixed lenses held by the lens frame 32. The lens frame 32 is formed in a substantially cylindrical shape, and a first lens 33a forming the observation window 15 is arranged on a distal end side inside the cylindrical shape. The lens group 33 is configured by arranging a second lens 33b, a third lens 33c, a fourth lens 33d and a fifth lens 33e behind the first lens 33a along an optical axis O in that order, and each lens is fixed to the lens frame 32 with adhesive or the like.

Note that apertures 34 and 35 are arranged behind the first lens 33a and behind the second lens 33b, respectively. The third lens 33c and the fourth lens 33d are arranged with a spacer 36 between the third lens 33c and the fourth lens 33d.

The observation optical system unit 31 above is combined with the image pickup device unit 40, and incident light incident via the lens group 33 is image-formed on a light receiving surface (an image pickup surface) of an image sensor 42 of the image pickup device unit 40. An optical image of an object is photoelectrically converted by the image sensor 42, and an image pickup signal obtained by the photoelectrical conversion is transmitted to a subsequent-stage signal processing circuit via a cable 70.

The image pickup device unit 40 includes a substantially cylinder-shaped image pickup device holding frame 41 holding the image sensor 42, and by inserting and fitting a proximal end side of the lens frame 32 of the observation optical system unit 31 into a distal end side inner diameter portion of the image pickup device holding frame 41 and watertightly bonding the proximal end side and the distal end side inner diameter portion to each other, the observation optical system unit 31 and the image pickup device unit 40 are combined.

The image sensor 42 is configured as an image pickup device package obtained by sealing a solid image pickup device composed of a CCD, a CMOS or the like with resin or the like. In the present embodiment, the image sensor 42 is configured as a small and lightweight chip size package (CSP) on which high density implementation is possible. In the image sensor 42, an image pickup surface 42a of the image pickup device is arranged on a front face side of the package. On the image pickup surface 42a side, a glass lid 43 for protection is bonded and fixed with adhesive or the like. Furthermore, a cover glass 44 for positioning is fixed to the glass lid 43 with adhesive or the like, and the cover glass 44 is fixed to a proximal end side inner diameter portion of the image pickup device holding frame 41 with adhesive or the like.

On a back face of the package, which is a rear face side of the image pickup surface 42a of the image sensor 42, an electrode portion 47 on which a plurality of electrode terminals are arranged is provided. A connection board 50 is connected to the electrode portion 47 of the image sensor 42, and a rigid circuit board 60 is connected to the connection board 50.

The connection board 50 is a board configured to relay electrical connection between the image sensor 42 and the circuit board 60. A connection portion to the image sensor 42 and a connection portion to the circuit board 60 are mutually electrically connected by a print pattern (not shown) formed in advance. In the present embodiment, the connection board 50 is composed of a flexible board made of a resin film or the like having flexibility.

The circuit board 60 is a circuit board on which various circuit chips of the image sensor 42 for driving and signal processing are implemented, and is formed as a rigid and high-strength board, which is a rigid body, such as a ceramic board. A plurality of lead wires 80 extended from the cable 70 are connected to a proximal end side of the circuit board 60. The cable 70 is insertedly arranged inside the endoscope 2 and electrically connected to the video processor 4 via the electrical connector 10a.

Note that a tubular reinforcing frame 45 made of metal is arranged being connected to a proximal end outer circumferential portion of the image pickup device holding frame 41. An outer cover 71 of the cable 70 is bound tight and fixed with a binding thread 86 composed of a metal wire, a nylon thread or the like on a distal end side.

A thermal contraction tube 46 as a protection tube covering the cable 70 up to the distal end side is provided on an outer circumference of the tubular reinforcing frame 45. A space formed by the reinforcing frame 45 and the thermal contraction tube 46 from a proximal end part of the image pickup device holding frame 41 is filled with protection material 90 such as insulating sealing resin for holding, reinforcing and protecting the image sensor 42.

Next, details of the connection portions between the image sensor 42, the connection board 50 and the circuit board 60 will be described.

Figure 3:
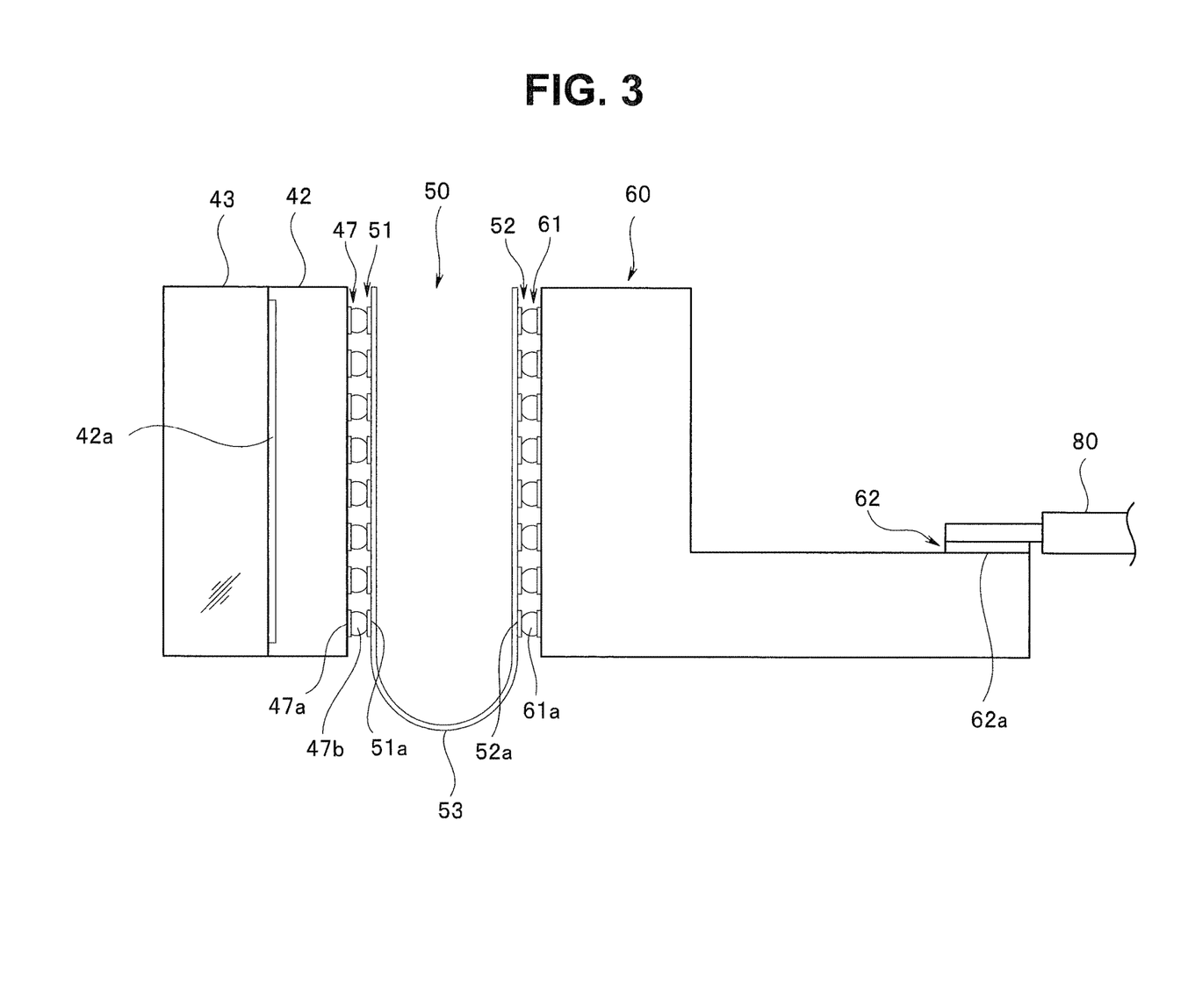
FIG. 3 is an explanatory diagram showing connection between an image sensor and a board according to the first embodiment of the present invention.

As shown in FIG. 3, the image sensor 42 including a CSP package has a configuration in which a plurality of electrode pads 47a are arranged in an array on the electrode portion 47 formed on the rear face side of the image pickup surface 42a. A spherical solder ball 47b made of solder is bonded to each electrode pad 47a of the electrode portion 47 to form a bump.

The connection board 50 includes a first land portion 51 and a second land portion 52 on both sides of a flexible board, and a plurality of lands 51a and a plurality of lands 52a to be electrode terminals are formed on the first land portion 51 and the second land portion 52, respectively. The lands 51a of the first land portion 51 are associated with the respective lands 52a of the second land portion 52 in advance, and connected by a print pattern not shown.

The circuit board 60 includes a first connection portion 61 to which the connection board 50 is connected, and a second connection portion 62 to which the cable 70 is connected. A plurality of electrode terminals 61a and a plurality of electrode terminals 62a are formed on the first connection portion 61 and the second connection portion 62, respectively. Each electrode terminal 61a of the first connection portion 61 is connected mainly to a terminal for drive output, image pickup signal input or the like to the image sensor 42 from each circuit part via the print pattern not shown, and each electrode terminal 62a of the second connection portion 62 is connected mainly to a terminal of each circuit part for signal input/output or the like to the video processor 4 via the print pattern not shown. Note that the first connection portion 61 is configured as a bump electrode similar to the electrode portion 47 of the image sensor 42.

The image sensor 42 and the connection board 50 are electrically connected by performing heat bonding of each of the solder balls 47b of the electrode portion 47 and each land 51a of the first land portion 51, or the like. The connection board 50 and the circuit board 60 are electrically connected by the plurality of lands 52a of the second land portion 52 being bonded to the respective electrode terminals 61a of the first connection portion 61 of the circuit board 60. To the respective electrode terminals 62a of the second connection portion 62 of the circuit board 60, a plurality of lead wires 80 extended from the cable 70 are bonded by soldering or with electrically conductive adhesive and electrically connected.

Here, the connection board 50 includes a curved portion 53 curved in a manner of being displaceable by an external force transmitted from the cable 70 via the circuit board 60, which is a rigid body, between the first land portion 51 and the second land portion 52. Due to the curved portion 53, it is possible to prevent an excessive load from being applied to a bonding surface between the image pickup surface 42a of the image sensor 42 and the glass lid 43 from the cable 70 side via the circuit board 60.

In the present embodiment, on the circuit board 60, an electrode arrangement surface of the first connection portion 61 and an electrode arrangement surface of the second connection portion 62 are orthogonal to each other, and the electrode arrangement surface of the first connection portion 61 is arranged facing an electrode arrangement surface of the electrode portion 47 of the image sensor 42. The connection board 50 interposed between the electrode portion 47 of the image sensor 42 and the first connection portion 61 of the circuit board 60 includes the curved portion 53 curved like a U-shaped groove between the first land portion 51 and the second land portion 52, and due to the curved portion 53, it is possible to reduce a load transmitted to the image sensor 42 from the cable 70 via the circuit board 60, which is a rigid body.

That is, if an external force acts on the second connection portion 62 of the circuit board 60 due to curving, torsion, tilt and the like of the cable 70, especially the image sensor 42 and the circuit board 60 generate heat as the endoscope 2 is used, and the protection material 90 around the image sensor 42 becomes soft. In such a situation, the circuit board 60, which is a rigid body, is displaced by the external force applied to the cable 70, and a load is applied to other parts arranged being connected to the circuit board 60.

Figure 4:
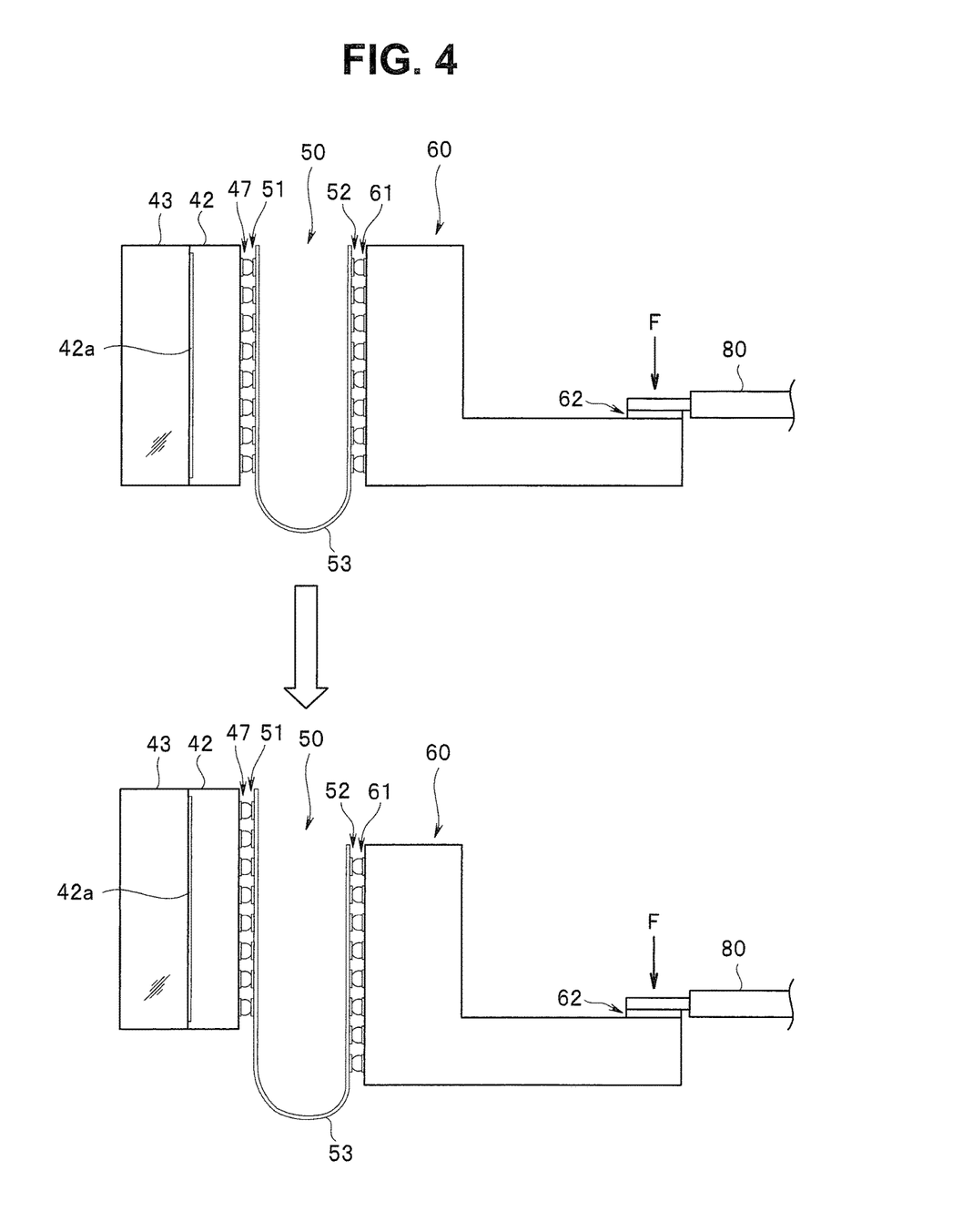
FIG. 4 is an explanatory diagram schematically showing an action of a load applied to the image sensor according to the first embodiment of the present invention.

For example, if an external force F acts in a direction orthogonal to an extension direction of the cable 70 as shown in FIG. 4, the whole circuit board 60, which is a rigid body, is displaced relative to the electrode portion 47 of the image sensor 42 by the external force F. On the connection board 50, in response to the displacement of the circuit board 60, the curved portion 53 is displaced, and the curved shape changes, between the first land portion 51 connected to the image sensor 42 and the second land portion 52 connected to the circuit board 60.

Therefore, even if the circuit board 60 is displaced by an external force, only a part of the connection board 50 near the curved portion 53 is displaced in response to the displacement, so that the external force can be absorbed and reduced. Thereby, it is possible to reduce a load by an external force transmitted to the image sensor 42 from the cable 70 via the circuit board 60. As a result, it does not happen that such an excessive force that causes detachment of a bonding layer between the image pickup surface 42a of the image sensor 42 and the glass lid 43 is applied to the bonding layer, and it is possible to effectively prevent occurrence of a trouble such as detachment.

In this case, though the protection material 90 such as sealing resin filled around the image sensor 42 and the curved portion 53 may be material of one kind, the protection material 90 may include first protection material 90a and second protection material 90b that is softer than the first protection material 90a as exemplified in FIG. 2. The second protection material 90b is arranged at least in a space formed by the curved portion 53.

In the case of forming the first and second protection materials 90a and 90b with resin material, resin softer than resin material as the first protection material 90a is used as resin material as the second protection material 90b. By arranging the soft resin material in the space formed by the curved portion 53, it is possible to cause the curved portion 53 to function more effectively.

As the second protection material 90b arranged in the curved portion 53, soft material such as sponge can be used instead of resin material. It is also possible to arrange nothing around the curved portion 53 and leave the space as a cavity.

Though the connection board 50 composed of a flexible board is folded in a U shape between the first land portion 51 and the second land portion 52 to form the curved portion 53 in the present embodiment, the curved portion 53 may be formed by causing the connection board 50 to be curved a plurality of times between the first land portion 51 and the second land portion 52.

Figure 5:
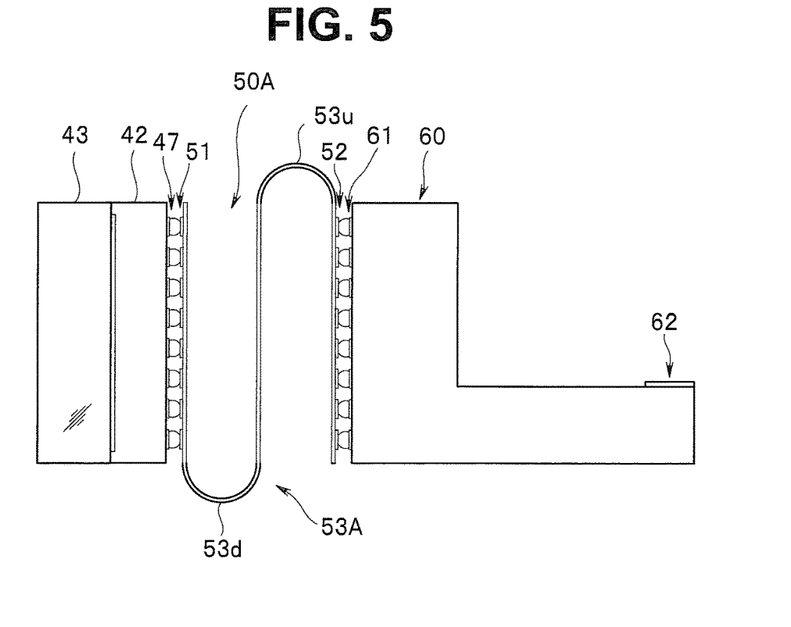
FIG. 5 is an explanatory diagram showing a first modification of a connection board according to the first embodiment of the present invention.

FIG. 5 shows a first modification of the connection board 50. A connection board 50A of the first modification is a flexible board that is vertically folded twice between the first and second land portions 51 and 52. That is, a curved portion 53A of the connection board 50A is formed by arranging two curved portions 53u and 53d formed by performing vertical curving twice between the first land portion 51 and the second land portion 52, and it is possible to reduce an external force more effectively by the two curved portions 53u and 53d.

Figure 6:
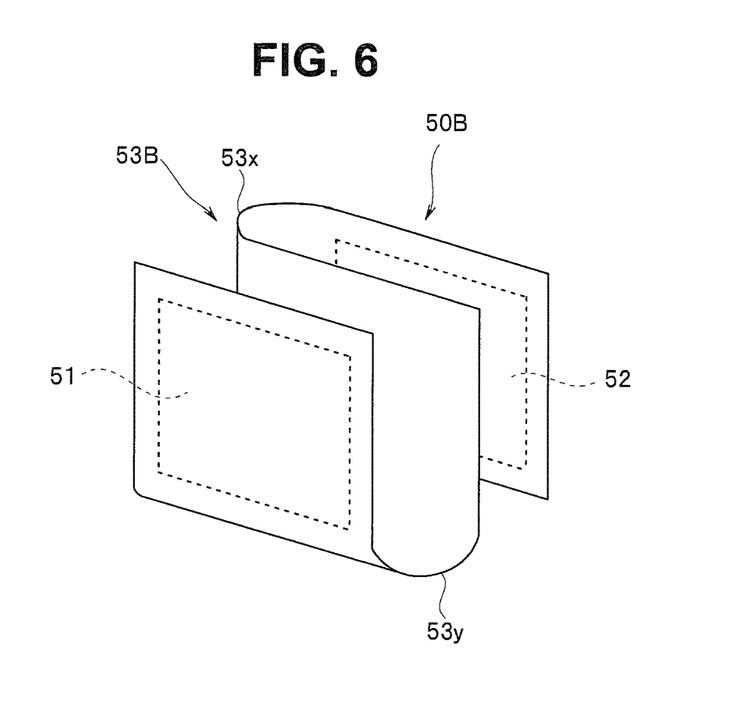
FIG. 6 is an explanatory diagram showing a second modification of the connection board according to the first embodiment of the present invention.

FIG. 6 shows a second modification of the connection board 50. A connection board 50B of the second modification is a flexible board that is folded twice in mutually different directions such as vertical and horizontal directions between the first and second land portions 51 and 52. A curved portion 53B of the connection board 50B is formed by arranging two curved portions 53x and 53y formed by performing curving twice vertically and horizontally between the first land portion 51 and the second land portion 52, and it becomes possible to reduce external forces from more directions.

Note that the connection board 50 (50A, 50B) may be formed by a rigid flexible board obtained by integrating a flexible board and a rigid board, and the curved portion 53 (53A, 53B) can be formed by causing a part having flexibility to be curved. It is also possible to use, for example, a metal board or the like having elasticity as the connection board 50. The curved portion 53 may be formed by sharply folding the metal board so that not a circular-arc shaped cross section but a ridge-valley shaped cross section is obtained.

Thus, in the present embodiment, for the image pickup unit in which the circuit board 60, which is a rigid body such as a ceramic board, is connected to the image sensor 42 configured as a CSP package, a load transmitted to the image sensor 42 via the circuit board 60, which is a rigid body, by curving, torsion, tilt and the like of the cable 70 can be reduced by the curved portion 53 of the connection board 50 interposed between the image sensor 42 and the circuit board 60. As a result, it is possible to reduce a load applied to the bonding layer between the image pickup surface 42a of the image sensor 42 and the glass lid 43 and to prevent detachment of the bonding layer.

Second Embodiment

Figure 7:
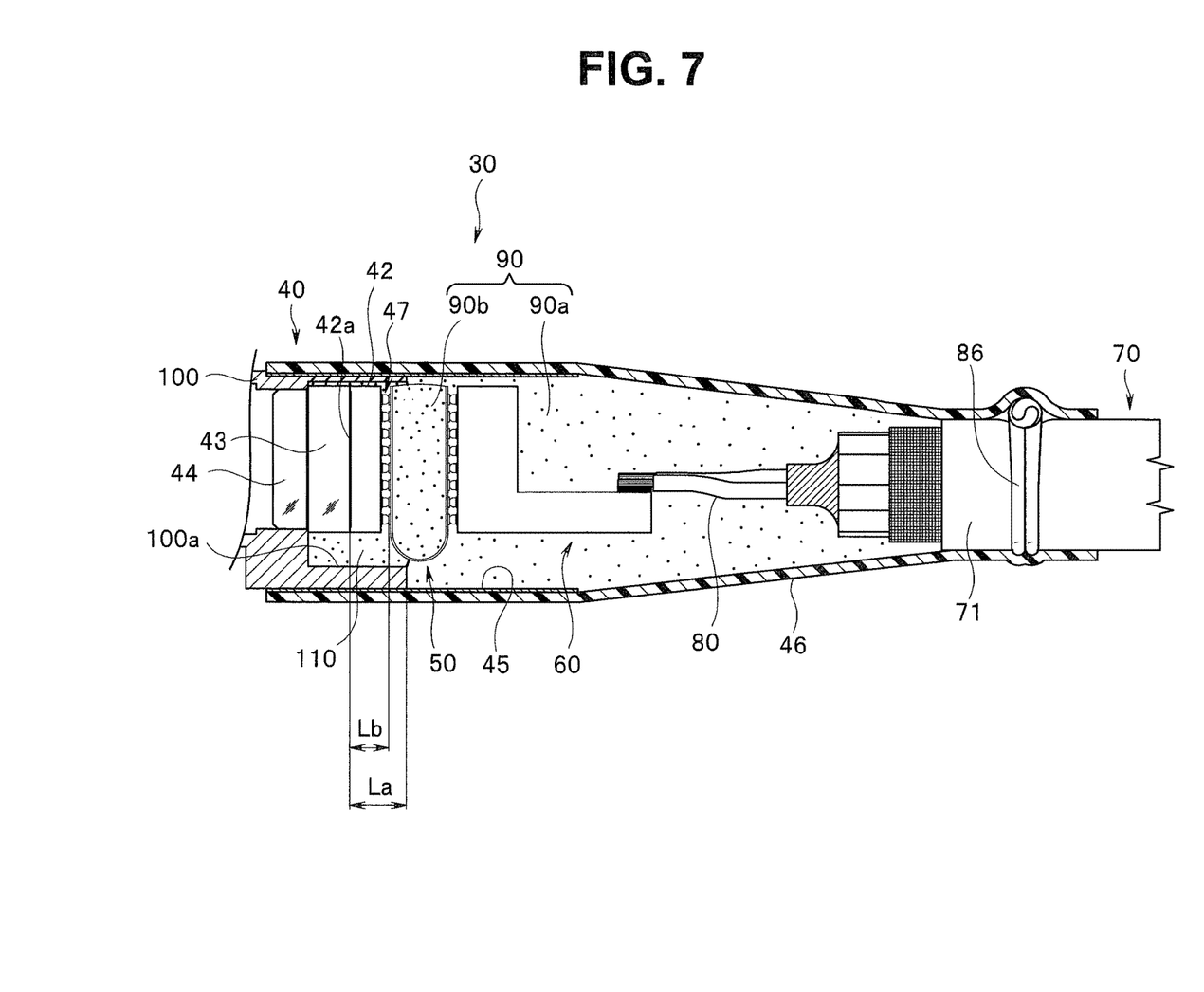
FIG. 7 is an explanatory diagram showing an image pickup device holding frame according to a second embodiment of the present invention.

Next, a second embodiment of the present invention will be described. The second embodiment is such that the shape of the image pickup device holding frame 41 holding the image sensor 42 is slightly changed, and an extending portion extending to the connection board 50 side is provided.

More specifically, an image pickup device holding frame 100 of the second embodiment extends on a proximal end side on which the cover glass 44 is fixed, and has an extending portion 100a including the glass lid 43 and the image sensor 42 and extending to a proximal end side relative to the image sensor 42.

More specifically, when a distance (a projection length) from a bonding surface between the cover glass 44 and the glass lid 43 to a distal end of the extending portion 100a is indicated by La, the projection length La of the extending portion 100a is set to be in a relationship of La>Lb relative to a distance Lb from the bonding surface between the cover glass 44 and the glass lid 43 to an electrode surface including the electrode portion 47 of the image sensor 42.

The extending portion 100a is formed in a tubular shape having such an extension length that covers the electrode portion 47 side of the image sensor 42 or as a part extended to a proximal end side relative to the image sensor 42 to form a nail shape, and protection material 110 is arranged inside the extending portion 100a. As the protection material 110, the first protection material 90a described in the first embodiment may be used. Otherwise, protection material such as resin material with a higher heat resistance may be used.

Since the projection length La of the extending portion 100a is set to be in the relationship of La>Lb relative to the electrode portion 47 of the image sensor 42, the image pickup device holding frame 100 of the second embodiment can, if a load larger than the load in the first embodiment is applied, receive the load by the extending portion 100a via the protection material 110.

Thus, in the second embodiment, even if a large load that cannot be reduced by the curved portion 53 of the connection board 50 is applied, the load can be received by the extending portion 100a via the protection material 110, and a load applied to the bonding layer between the image pickup surface 42a of the image sensor 42 and the glass lid 43 can be reduced, in comparison with the first embodiment.

What is claimed is:
1. An image pickup unit comprising:
an image sensor comprising an image pickup surface being arranged on a front face side and an electrode portion being arranged on a back face side;
a connection board comprising a first land portion and a second land portion, the first land portion being connected to the electrode portion of the image sensor;
a rigid circuit board comprising a first connection portion and a second connection portion, the first connection portion and the second connection portion being arranged so as to be orthogonal to each other, the first connection portion being connected to the second land portion of the connection board;
a cable connected to the second connection portion of the circuit board; and
protection material arranged around the connection board and the image sensor; wherein
the image sensor and the circuit board are arranged such that the electrode portion of the image sensor and the first connection portion face each other;
the connection board comprises a curved portion between the first land portion and the second land portion, the curved portion being curved in a manner of being displaceable relative to the electrode portion of the image sensor by an external force that acts in a direction orthogonal to an extension direction of the cable; and the protection material includes first protection material and second protection material softer than the first protection material, the second protection material being arranged at least inside the curved portion.

2. The image pickup unit according to claim 1, wherein the connection board comprises a single flexible board having flexibility, and the curved portion is formed by folding the single flexible board a plurality of times in directions different from each other.

3. The image pickup unit according to claim 1, wherein a holding frame holding the image sensor is provided with an extending portion extending to a proximal end side relative to the image sensor, and the protection material is filled inside the extending portion.

4. The image pickup unit according to claim 2, wherein the curved portion of the connection board is formed by causing the single flexible board to be curved in a form of a U-shaped groove at a portion of the single flexible board between the first land portion and the second land portion such that the first land portion and the second land portion are arranged so as to face each other.

5. An endoscope comprising:
an insertion portion configured to be inserted into a subject, and
an image pickup portion provided at a distal end of the insertion portion and configured to pick up an image of an inside of the subject,
the image pickup portion comprising:
an image sensor comprising an image pickup surface being arranged on a front face side and an electrode portion being arranged on a back face side;
a connection board comprising a first land portion and a second land portion, the first land portion being connected to the electrode portion of the image sensor;
a rigid circuit board comprising a first connection portion and a second connection portion, the first connection portion and the second connection portion being arranged so as to be orthogonal to each other, the first connection portion being connected to the second land portion of the connection board;
a cable connected to the second connection portion of the circuit board and extended toward a proximal end side of the insertion portion; and
protection material arranged around the connection board and the image sensor; wherein
the image sensor and the circuit board are arranged such that the electrode portion of the image sensor and the first connection portion face each other;
the connection board comprises a curved portion between the first land portion and the second land portion, the curved portion being curved in a manner of being displaceable relative to the electrode portion of the image sensor by an external force that acts in a direction orthogonal to an extension direction of the cable; and
the protection material includes first protection material and second protection material softer than the first protection material, the second protection material being arranged at least inside the curved portion.

* * * * *